United States Patent [19]

Holtkamp

[11] Patent Number: Plant 5,600

[45] Date of Patent: Dec. 17, 1985

[54] AFRICAN VIOLET PLANT NAMED IMPROVED OREGON

[75] Inventor: Reinhold Holtkamp, Isselburg, Fed. Rep. of Germany

[73] Assignee: Gessellschaftsvertrag uber die Ergindergemeinschaft "OPTIMARA", Rees Haffen, Fed. Rep. of Germany

[21] Appl. No.: 568,439

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet plant named Improved Oregon, characterized by its vigorous growth habit, abundance of upright wire-like flower stems each of which produces 7–9 flowers having frilled edges and intensive pink flower color, profuse flowering, long lasting and non-dropping flowers, and by its dark green, generally round and finely serrated leaves.

1 Drawing Figure

1

The present invention comprises a new and distinct cultivar of African violet plant, botanically known as *Saintpaulia ionantha,* and named Improved Oregon.

The new cultivar was referred to during the breeding and selection process by the designation G 93/XXIII, and is a product of a planned breeding program. The basic purpose of the breeding program was to improve certain characteristics of the cultivar Oregon, disclosed in my U.S. Plant Pat. No. 4,498.

The new cultivar was originated from a cross made in a controlled breeding program in Isselburg, West Germany. The female, or seed parent was a cultivar designated C 165/2X. The male, or pollen parent was a cultivar designated F III Pink frilled.

The new cultivar Improved Oregon was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Improved Oregon has not been observed under all possible environmental conditions. The phenotype may vary significantly with variations in environment such as temperature, light intensity and day length. The following observations, measurements and values describe the new cultivar as grown in Isselburg, West Germany, and Nashville, Tenn. under the greenhouse conditions which closely approximate those generally used in commercial practice.

The following traits have been repeatedly observed and are determined to be basic characteristics of Improved Oregon, which in combination distinguish this African violet as a new and distinct cultivar:

1. Twelve or more strong and upright, wire-like flower stems, each of which carries 7–9 flowers.
2. Very delicately frilled flower edges.
3. Intensive pink flower color with a relatively darker pink center.
4. Profuse flowering, with the flowers being long lasting and non-dropping.
5. Dark green, generally round and serrated leaves.

2

The new cultivar is most similar to Oregon, referred to above and upon which it was intended to improve. In comparison to Oregon, the new cultivar has a more intensive pink flower color, the stems are greater in number and stronger, with the abundance of stems producing a substantially more floriferous cultivar.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 10:00 A.M. on December 1 in Nashville, Tenn. When finished under relatively cool conditions, the flower color will be more intense, and when finished under relatively high temperatures, the flower color has a tendency to slightly fade.

Botanical classification: *Saintpaulia ionantha,* Ramat. cv. IMPROVED OREGON.

Parentage:

*Male parent.*—F III Pink frilled.

*Female parent.*—C 165/2X.

Propagation: The new cultivar holds its distinguishing characteristics through successive propagations by leaf cuttings and by division of shoots.

Plant: From 7 cm. to 9 cm. tall when grown in pots, and approximately 25 cm. in diameter when fully grown.

*Leaves.*—General form: Round. Diameter: 55–70 mm. Texture: Leather-like. Aspect: Velvety; hairy; slightly shiny; indented. Veins: Well pronounced; light green to brownish green. Color (upperside): Yellow green 147 between A-B. Color (underside): Yellow green 148D. Petiole: Brownish; hairy.

*Flowers.*—Buds; Ball shape, greenish pink. Sepals: 5; hairy. Color: Brownish. Calyx: Flat funnel. Aspect: Spear shape, hairy. Peduncle: Short, wire-like, upright.

*Individual flowers.*—Size: 35 mm. Color: Upperside: Red purple Group 73B, center 73A. Underside: Red purple Group 65A. Borne: On upright wire-like flower stems. Shape: Violet shape; 2 small and 3 large petals; single form. Corolla: Very profuse and tight; well above the leaves. Flowering time: In 9–10 weeks after potting, a saleable plant having a full bouquet is formed.

*Reproductive organs.*—Anthers: 2 formed by 4 cells. Filaments: Bright green. Styles: Dark pink with white stigma. Pollen color: Yellow.

*Roots.*—White when young and active; brownish when older.

*Disease resistance.*—Good as experienced to date.

General observations:

Improved Oregon has a vigorous growth habit, with the plant being fully developed in approximately 10 weeks. Up to 12 or more flower stems are produced, each of which carry 7 or more frilled, red-purple flowers having darker flower centers. The abundance and strength of the flower stems produces a very compact and profuse flower head, with the flowers being long lasting and non-dropping. The leaves are uniquely characterized by the degree of edge serration.

I claim:

1. A new and distinct cultivar of African violet plant named Improved Oregon, as illustrated and described, and particularly characterized by its vigorous growth habit, abundance of upright wire-like flower stems each of which produces 7–9 flowers having frilled edges and intensive pink flower color, profuse flowering, long lasting and non-dropping flowers, and by its dark green, generally round and finely serrated leaves.

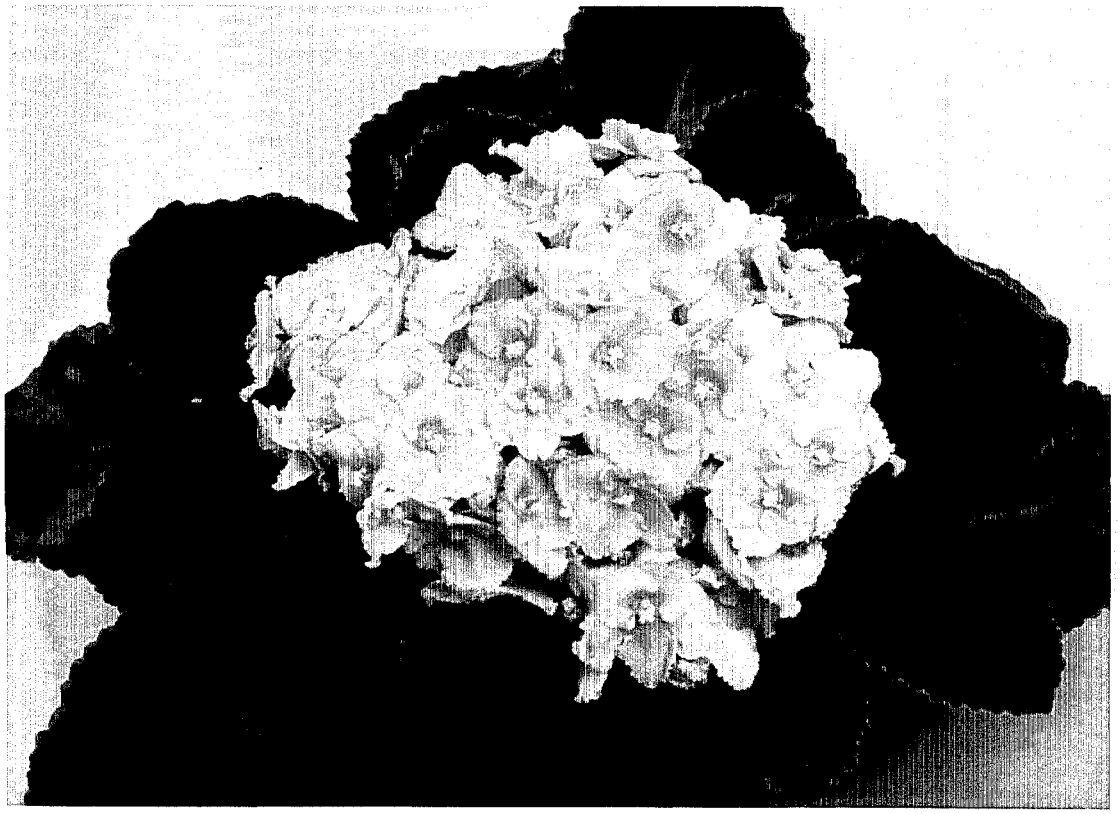

* * * * *